United States Patent [19]

Williams et al.

[11] 4,006,017
[45] Feb. 1, 1977

[54] PHOTOCONDUCTIVE COMPOSITION, ARTICLE AND PROCESS

[75] Inventors: David J. Williams, Fairport; William W. Limburg, Penfield; James M. Pearson, Webster, all of N.Y.

[73] Assignee: Xerox Corporation, Stamford, Conn.

[22] Filed: Feb. 10, 1975

[21] Appl. No.: 548,453

Related U.S. Application Data

[63] Continuation-in-part of Ser. No. 454,486, March 25, 1974, abandoned.

[52] U.S. Cl. ................................. 96/1 R; 96/1.5; 260/315; 260/240.4
[51] Int. Cl.$^2$ ........................................ G03G 5/04
[58] Field of Search ............. 96/1.3, 1 R; 260/315, 260/240.4

[56] References Cited

UNITED STATES PATENTS

| | | | |
|---|---|---|---|
| 3,287,115 | 11/1966 | Hoegl | 96/1.5 |
| 3,536,484 | 10/1970 | Dowden | 96/1.5 |
| 3,542,546 | 11/1970 | Fox | 96/1.5 C |
| 3,844,715 | 10/1974 | Renfrew | 260/315 |

*Primary Examiner*—David Klein
*Assistant Examiner*—John L. Goodrow
*Attorney, Agent, or Firm*—James J. Ralabate; James Paul O'Sullivan; John H. Faro

[57] ABSTRACT

Photoconductive composition comprising an insulating polymeric matrix and a compound of the formula

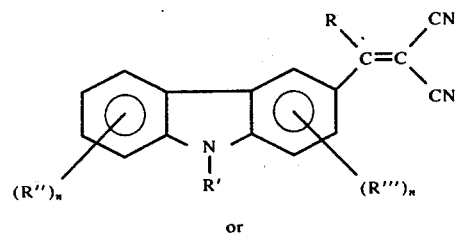

or

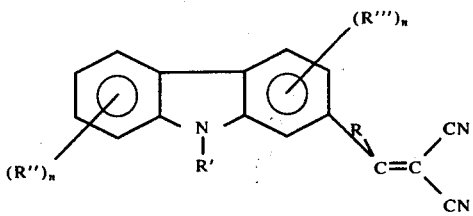

wherein R is hydrogen or nitrile; and R', R'' and R''' are independently selected from an aliphatic hydrocarbon radical having from about 1 to about 10 carbon atoms; phenyl; or substituted phenyl, said phenyl substituents being capable of releasing electrons to relatively electron deficient centers within the compound; amino; diarylamino; dialkylamino or alkoxy; and n can range from 0 up to the potential number of positions of substitution on the aromatic ring system.

These compositions have good spectral response in the visible region of the electromagnetic spectrum and are suitable for use in electrostatographic imaging members and methods.

15 Claims, No Drawings

PHOTOCONDUCTIVE COMPOSITION, ARTICLE AND PROCESS

CROSS-REFERENCE TO RELATED APPLICATION

This application is a continuation in part of copending application, Ser. No. 454,486, filed Mar. 25, 1974 and now abandoned.

BACKGROUND OF THE INVENTION

1. Field of the Invention

This invention relates to a composition, an article and a method. More specifically, the compositions embraced within the scope of this invention are highly efficient photogenerator materials and are thus suitable for use in electrophotographic imaging members and methods.

2. Description of the Prior Art

The formation and development of images on the imaging surfaces of photoconductive materials by electrostatic means is well-known. The best known of the commercial processes, more commonly known as xerography, involves forming a latent electrostatic image on the imaging surface of an imaging member by first uniformly electrostatically charging the surface of the imaging layer in the dark and then exposing this electrostatically charged surface to a light and shadow image. The light struck areas of the imaging layer are thus rendered relatively conductive and the electrostatic charge selectively dissipated in these irradiated areas. After the photoconductor is exposed, the latent electrostatic image on this image bearing surface is rendered visible by development with a finely divided colored electroscopic material, known in the art as "toner". This toner will be principally attracted to those areas on the image bearing surface which retain the electrostatic charge and thus form a visible powder image.

The developed image can then be read or permanently affixed to the photoconductor where the imaging layer is not to be reused. This latter practice is usually followed with respect to the binder-type photoconductive films (e.g. zinc oxide/insulating resin binder) where the photoconductive imaging layer is also an integral part of the finished copy, U.S. Pat. Nos. 3,121,006 and 3,121,007.

In so-called "plain paper" copying systems, the latent image can be developed on the imaging surface of a reusable photoconductor or transferred to another surface, such as a sheet of paper, and thereafter developed. When the latent image is developed on the imaging surface or a reusable photoconductor, it is subsequently transferred to another substrate and then permanently affixed thereto. Any one of a variety of well-known techniques can be used to permanently affix the toner image to the copy sheet, including overcoating with transparent films, and solvent or thermal fusion of the toner particles to the supportive substrate.

In the above "plain paper" copying systems, the materials used in the photoconductive layer should preferably be capable of rapid switching from insulating to conductive to insulating state in order to permit cyclic use of the imaging surface. The failure of a material to return to its relatively insulating state prior to the succeeding charging/imaging sequence will result in an increase in the rate of dark decay of the photoconductor. The phenomenon, commonly referred to in the art as "fatigue" has in the past been avoided by the selection of photoconductive materials possessing rapid switching capacity. Typical of the materials suitable for use in such a rapidly cycling imaging system include anthracene, sulfur, selenium and mixtures thereof (U.S. Pat. No. 2,297,691); selenium being preferred because of its superior photosensitivity.

In addition to anthracene, other organic photoconductive materials, most notably, poly(N-vinylcarbazole), have been the focus of increasing interest in electrophotography, U.S. Pat. No. 3,037,861. Until recently, neither of these organic materials have received serious consideration as an alternative to such inorganic photoconductors as selenium, due to fabrication difficulties and/or to a relative lack of speed and photosensitivity within the visible band of the electromagnetic spectrum. The recent discovery that high loadings of 2,4,7-trinitro-9-fluorenone in polyvinylcarbazoles dramatically improves the photoresponsiveness of these polymers has led to a resurgence in interest in organic photoconductive materials U.S. Pat. No. 3,484,237. Unfortunately, the inclusion of high loadings, of such activators can and usually does result in phase separation of the various materials within such a composition. Thus, there will occur within these compositions regions having an excess of activator, regions deficient in activator and regions having the proper stoichiometric relation of activator to photoconductor. The maximum amount of activator that may be added to most polymeric photoconductive materials without occasioning such phase separation generally will not exceed in excess of about 6 to about 8 weight percent.

One method suggested for avoiding the problems inherent in the use of such activators in conjunction with polymeric photoconductors, is the direct incorporation of the activators into the polymeric backbone of the photoconductor, U.S. Pat. No. 3,418,116. In this patent is disclosed the copolymerization of a vinyl monomer having an aromatic and/or heterocyclic substituent capable of an electron donor function with a vinyl monomer having an aromatic and/or heterocyclic substituent capable of an electronic acceptor function. The spatial constraint placed upon these centers of differing electron density favors their charge transfer interaction upon the photoexcitation of such a composition. These so-called "intramolecular" charge transfer complexes, more accurately designated "intrachain" charge transfer complexes, are believed to function substantially the same as charge transfer complexes formed between small activator molecules and a photoconductive polymer. The fact that the electron donor function and an electron acceptor function are on a common polymeric backbone does not apparently change the $\pi-\pi$ charge transfer interaction, but merely increases the probability of it occuring. Unfortunately, the preparation of such polymers from vinyl monomers having electron donor centers and vinyl monomers having electron acceptor centers is often beset with difficulty.

The preparation of non-polymeric photoconductive tricyanovinyl compounds, wherein an electron rich center and an electron deficient center are contained within a common molecule, is disclosed in U.S. Pat. No. 3,721,552 (corresponding Australian patent application Ser. No. 36,760/68, published Oct. 10, 1969). Patentee discloses the preparation of photoconductive "binder" layers by dispersing from about 10 to about 90 parts by weight of his novel tricyanovinyl compounds in about 90 to about 10 parts by weight resin binder. The binder resins which can be used in preparation of the photoconductive insulating layer must have an electrical volume resistivity in excess of $10^8$ ohm-cm. Virtually any of the binders traditionally employed in preparation of electrophotographic imaging members are reportedly suitable in the preparation of these binder layers. Insofar as the preferred weight ratio of photoconductive particles to binder resin is 1:1, it is apparent that Patentee does not appreciate that sufficiently lower loadings of such compounds in a charge transport matrix can produce results equivalent to his preferred composition. By minimizing the amount of photoconductive compound needed to achieve satisfactory photoresponse, the inherent physical properties of the film forming binder resin are preserved (e.g. flexibility, adhesion, and free surface energy).

It is the principal object of this invention to provide a novel class of photogenerator compounds which are suitable for use in photoconductive compositions.

It is another object of this invention to provide a photogenerator compound having a high extinction coefficient.

It is yet another object of this invention to provide a photogenerator compound wherein charge transfer interaction between a donor and acceptor site occur independent of the relative concentration of the photogenerator compounds in the resin.

It is yet a further object of this invention to provide a photoconductive composition having broad spectral response in the visible region of the electromagnetic spectrum.

Further objects of this invention include providing imaging members wherein the imaging layer is prepared from the above composition and the use of said imaging members in an imaging method.

SUMMARY OF THE INVENTION

The above and related objects are achieved by providing a photoconductive composition comprising an insulating polymeric matrix and a compound of the formula

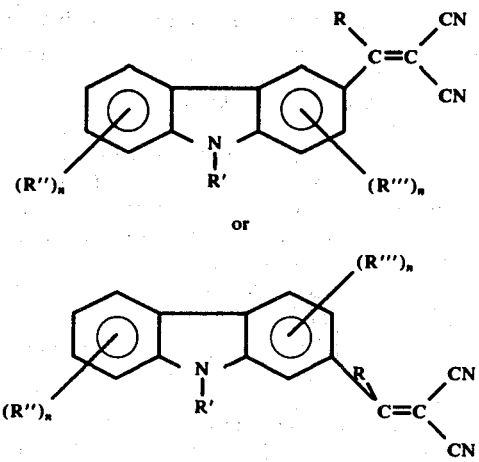

wherein R is hydrogen or nitrile; and R', R" and R''' are independently selected from an aliphatic hydrocarbon radical having from about 1-10 carbon atoms; phenyl; or substituted phenyl wherein said substituents are capable of releasing electrons to relatively electron deficient centers within the compound amino; diarylamino; dialkylamino or alkoxy; n can range from 0 up to the potential number of positions of substitution on the aromatic ring system.

In the preferred embodiments of this invention, the above polymeric matrix is also capable of rapid and efficient transport of charged carriers generated during photoexcitation of the above compound. In such preferred embodiments of this invention, the concentration of photogenerator compound is generally less than 50 weight percent.

DESCRIPTION OF THE INVENTION INCLUDING PREFERRED EMBODIMENTS

The composition of this invention can be prepared by combining one or more of the hereinafter described photogenerator compounds and the various other materials comprising the insulating polymeric matrix in a common solvent and casting or coating the resulting solution on an appropriate (preferably conductive) substrate. The relative concentration of photogenerator compound to matrix materials in such compositions will vary with the transport capabilities of the polymeric matrix. The insulating polymer matrices suitable for use in this invention can be either "electronically active" or "electronically inert". The classification of the matrix as active or inert is determined by the relative ability of the matrix, when used in conjunction with the photogenerator, to transport charge. Those materials which are capable of efficient transport of at least one species of photogenerated charge carrier are considered electronically active and the insulating polymeric matrix classified as an "active matrix". Conversely, those materials which do not exhibit transport of at least one species of photogenerated charge carrier are regarded as electronically inert and the insulating polymeric matrix classified as an "inert matrix". Electronic activity (or inertness) of a matrix is, therefore, intended to be descriptive of two separate events, both of which must occur; the capacity (or incapacity) of the matrix to permit injection of photogenerated charge carriers into its bulk and the capacity (or incapacity) of the matrix to transport such injected charge carriers through its bulk without trapping.

Virtually, any of the polymeric binders disclosed in the prior art can be used in combination with the photogenerator compounds disclosed herein. Representative of the electronically inert binders suitable for use in the compositions of the invention include epoxy resins, poly(vinylchloride), poly(vinylacetates), poly(styrene), poly(butadiene), poly(methacrylates), poly(acrylics), poly(acrylonitriles), silicone resins, chlorinated elastomers, phenoxy resins, phenolic resins, epoxy-phenolic copolymers, epoxy/urea/formaldehyde terpolymers, epoxy/melamine/formaldehyde resins, poly(carbonates), poly(urethanes), poly(amides), saturated poly(esters) copolymers and blends thereof. Electronically active polymers which can be used as the matrix for the photogenerator compound include poly(N-vinylcarbazole), poly(2-vinylcarbazole), poly(3-vinylcarbazole), poly(vinylpyrene), poly(vinylnaphthalene), poly(2-vinylanthracene) and poly(9-vinylanthracene). Electronically active matrices can also be formed by combination of one or more of the above electronically inert polymers with one or more of the above electronically active polymers. The method of combination of such electronically distinct polymers can include copolymeriation (random, graft, block, etc.), formation of an interpenetrating polymer network and polymer blending. Alternatively, an electronically inert polymer matrix can be rendered an efficient transporter of charge carriers by the incorporation within a film of such materials so called "small molecules" capable of an efficient carrier transport. The term, "small molecules", is inclusive of single molecules and low molecular weight polymers. These small molecules can be added to the casting or coating solution during formation of the polymeric matrix or can be subsequently introduced into the matrix by swelling of the polymeric materials of the matrix with a solution containing the small molecule compounds. Upon evaporation of the liquid phase of the solution, the small molecules will remain entrapped within the polymeric matrix thus enhancing charge carrier transport properties of this insulating film. These small molecules can also be added to active polymeric matrices in order to enhance the transport of charge carriers not readily transported by the electronically active polymer. For example, Lewis Acid can be added to a photoconductive polymer such as poly(N-vinylcarbazole) in order to improve electron transport. Representative of small molecule additives, which can be added to either an electronically active or inert polymer matrix to facilitate hole (+) transport include pyrene, anthracene, carbazole, triphenylamine, naphthalene, julolidine, indole and perylene. Small molecule additive, which can be incorporated into either an electronically active or inert polymer matrix to facilitate electron (−) transport include anthracene, fluorenone 9-dicyanomethylene-fluorene, the nitro derivatives of fluorenone, the nitro derivatives of 9-dicyanomethylene-fluorene and chloranil. Both hole and electron small molecule transport materials can be used in combination with one another in inert polymers. A number of the above small molecules are known to form charge transfer complexes with both the inert and active polymer systems and some absorption by the matrix complex is permitted provided that the absorptivity of the resulting change transfer complex does not appreciably compete with the photogenerator compound to the extent that the absorption band of the composition is dominated by the absorption band of the complex. It is also understood that the absorptivity of the charge transfer complex must not be capable of shielding the photogenerator compound from incident radiation.

The photogenerator compounds of this invention, which satisfy the previously set forth structural formula, are part of a unique class of compounds that have both an electron withdrawing group and an electron releasing group connected to one another through a spatially constraining linkage thereby insuring that during photoexcitation of the polymeric matrix containing such compounds, the electronic transition moment from ground to excited state and flow of charge between said groups are colinear. Thus, the generation of charge carriers upon photoexcitation said compounds is highly efficient even at very low concentrations ($<\sim 6$ weight percent). Of course, at such low loadings the polymeric matrix must be electronically active in order to transport the carriers generated during exposure to electromagnetic radiation. In the preferred embodiments of this invention the concentration of photogenerator compound in an electronically active matrix can range from as low as about 0.1 to about 6 weight percent and yet provide satisfactory electrophotographic response. At such low concentrations the photoconductive composition can be described as a solid solution, i.e. a single phase composition formed between the photogenerator compound and the polymeric materials of the matrix in which homogeneity is not due to compound formation, *Van Norstrand's Scientific Encyclopedia*, 4th Ed., D. Van Norstrand Company Inc., p. 1651 (1968). Of course, where small molecules are added to polymeric materials to enhance transport of one or both species of charge carriers, the homogeneity of the composition may be altered somewhat At concentrations in excess of 6 weight percent (up to about a maximum of about 99.9 weight percent) the tendency for crystallization of the photogenerator compound within the matrix will increase. As the extent of crystallization increases, the physical properties of the polymer matrix will become impaired and the ability of the photoconductive composition to hold charge will also show progressive decline.

As indicated previously, the compositions of this invention can be readily prepared by simply combining the photogenerator compound and the film-forming insulating polymer in the proper relative proportions in a common solvent and thereafter casting or coating the resulting solution on an appropriate substrate. The amount of material coated on such substrates should be sufficient to provide a dry film having a thickness in the range of from about 0.1 to about 200 microns; the precise thickness being determined by the end use of said member. Any of the substrates traditionally used in preparation of electrophotographic imaging members can be coated with the above solution. Typical of substrates which are suitable in this regard include aluminum, chromium, nickel, brass, metallized plastic film, metal coated plastic film (e.g. aluminized Mylar) and conductive glass (e.g. tin oxide coated glass-NESA glass).

Upon preparation of an electrophotographic imaging member from the materials described above, said member can be used in standard electrophotographic imaging methods by simply sensitizing the surface of the photoconductive insulating layer of said member followed by exposure of the sensitized surface to a light and shadow image pattern. Where the photogenerator compound is dispersed in an electronically active polymer matrix, the wavelength of activating electromagnetic radiation should preferably be within the wavelength of substantial spectral response of the photogenerator compound and outside the range of substantial spectral response of the electronically active polymer matrix. Upon formation of a latent electrostatic image on said member, the image may be transferred to another substrate or developed directly on said imaging layer and thereafter transferred. Where one or more of such photogenerator compounds are incorporated within an electronically active polymer or an electronically active polymer containing a small molecule compound, the absorption spectrums of the composition are characteristic of the individual components of the composition, thus, indicating no discernable interaction between the photogenerator compound and the matrix.

In those compositions where the relative concentration of photogenerator compound adversely alters the charge storage capacity of the composition, films prepared from such compositions can be overcoated with an insulating (electronically "inert") polymer film. The dielectric thickness of this overcoating must be sufficient to support at least some, if not entire, sensitizing charge. Such overcoated imaging members are suitable for use in induction imaging systems of the type disclosed in U.S. Pat. Nos. 3,324,019 (to Hall), 3,676,117 (to Kinoshita) and 3,653,064 (to Inoue)—all of which are hereby incorporated by reference in their entirety. In the imaging system described by Inoue, the insulating overcoating is subjected to uniform corona charging in the light (the polarity of the charge being immaterial). The sensitized imaging member is now exposed to image information simultaneous with corona charging to opposite polarity. The imaged member is thereafter exposed to blanket illumination and a latent image thus produced developed with charged electroscopic toner particles and thereafter transferred to a receiving sheet.

The Examples which follow further define, describe and illustrate preparation and use of the compositions of this invention. Methods of preparation and evaluation of said compositions are standard or as hereinbefore described. Parts and percentages appearing in such Examples are by weight or otherwise indicated.

EXAMPLE I

Preparation of N-ethyl-3-tricyanovinylcarbazole

About 1 gram ($5.24 \times 10^{-3}$ moles) N-ethyl carbazole and 20 milliliters of dimethylformamide are placed in a 50 milliliter one neck flask equipped with a magnetic stirring bar and a nitrogen inlet tube. The flask is purged of air with nitrogen, the contents of the flask agitated and about 0.67 grams ($5.24 \times 10^{-3}$ moles) of tetracyanoethylene introduced into the flask. Upon the admixture of these materials the contents of the flask turns deep blue. This mixture is heated to 100° C for 20 hours, the contents of the flask poured into 60 milliliters of water at room temperature and the redish brown crystals thereby precipitated isolated from the solution by filtration and washed with ethanol. Yield: 1.13 grams brick red crystals m. p. 239°–241° C. Analysis: calculated, carbon 77, hydrogen 4.08, nitrogen 18.92; actual, carbon 77.24, hydrogen 4.07, nitrogen 18.78.

EXAMPLE II

Preparation of N-ethyl-3-dicyanovinylcarbazole

About 11.1 grams (0.05 moles) N-ethyl carbazole-3-carboxaldehyde, about 3.1 grams (0.05 moles) malononitrile, about 1 milliliter glacial acetic acid, about 0.35 grams ammonium acetate and about 40 milliliters benzene are heated to boiling under reflux conditions for about 30 minutes. The liquid portion of this mixture is separated from the brown colored solution by rotary evaporation, the solid residues twice recrystallized with glacial acetic acid washed with ethanol and dried in a vacuum oven. Yield: 7.0 grams of bright yellow needle like crystals m.p. 164°–165° C.

About 5 parts by weight N-ethyl-3-dicyanovinylcarbazole and 95 parts by weight poly(N-vinylcarbazole) are dissolved in tetrahydrofuran and draw coated on an aluminized Mylar substrate. The coated substrate is now transferred to a vacuum oven and allowed to remain there overnight. Sufficient solution is transferred to the substrate to provide a polymer coating having a dry film thickness of about 35 microns. The polymer becomes intensely colored upon admixture with the photogenerator compound, however, remains substantially homogenous. The photoconductive insulating layer thus produced is sensitized by corona charging to a negative potential of about 600 volts. This sensitized surface is exposed through a quartz glass transparency with a 100 watt tungsten lamp from a distance of 50 centimeters for an interval sufficient to selectively discharge the exposed surface of the photoconductive insulating layer and thereby form a latent electrostatic image. This latent electrostatic image is developed with positively charged toner particles and the toner image thereafter transferred to a sheet of untreated paper. Toner residues remaining on the surface of the film are removed by wiping with a soft cotton cloth. Prior to resensitization, the photoconductive insulating layer is subjected to blanket exposure with ultraviolet light simultaneous with positive corona charging. The copying cycle is then repeated. Copy quality remains good and is reproducible.

EXAMPLE III

Preparation of N-ethyl-2-tricyanovinylcarbazole

A heterogenous mixture comprising about 150 grams (0.75 moles) of 2-nitrobiphenyl, 6.6 grams ferric chloride and about 170 milliliters of water are placed in a 1000 milliliter 3-neck flask equipped with an addition funnel, an air driven stir and a reflux condenser. The contents of the flask are heated to and maintained at a temperature of between 35° and 40° C with rapid agitation as 120 grams (0.75 moles) of liquid bromine are added by dropwise addition. After this addition is complete, the contents of the flask are stirred for an additional 2 hours at the above temperature. Heating of the contents of the flask now ceases and the mixture is allowed to remain overnight a room temperature with peridic stirring. The following day the mixture is reheated over a steam bath for approximately 4 hours, after which time the condenser is opened to allow for the escape of excess bromine. The contents of the flask are taken up in ether and washed with saturated sodium carbonate solution. The ether solution is now dried over anhydrous sodium sulfate, and solvents removed from the reaction product by rotary evaporation to an orange-yellow viscous mass. This viscous material is separated into fractions by standard distillation techniques. The fraction boiling at 170° is recycled and the fraction having a boiling point in excess of 170° collected and titrated with ethanol to initiate crystallization. The crystals are collected on a Buchner funnel and washed with ethanol. These crystals are identified as 2-nitro-4'-bromobiphenyl, m. p. 64°–66° C. This product is now converted to 2-bromocarbazole by reductive cyclization. This is achieved by combining about 45 grams (0.16 moles) of 2-nitro-4'-bromobiphenyl and about 107.7 grams (0.648 moles) triethylphosphite in a 500 milliliter 3necked flask equipped with a magnetic stirring bar, a nitrogen gas inlet and a reflux condenser. The contents of the flask are blanketed with nitrogen and heated to 160° C for 15 hours. The contents of the flask are then allowed to cool to room temperature, and thereafter poured into a mixture comprising 1200 milliliters methanol and 120 milliliters water. The desired product 2-bromocarbazole, precipitates out of solution and is separated therefrom by filtration. Yield: 24.4 grams m. p. 243°–246° C.

This product is alkylated at the N position by combining 20.6 grams (0.082 moles) thallous ethoxide, 20.1 grams (0.082 moles) 2-bromo-carbazole, 2.5 grams (0.34 moles) dimethylformamide and 100 milliliters tetrahydrofuran in a reaction vessel and heating the resulting mixture to 55° C for an interval of 45 minutes. During this time the contents of the flask turn a deep tan color. About 13.4 grams (0.86 moles) ethyliodide is now added to the mixture whereupon the color changes from tan to yellow. Following such addition the contents of the reaction vessel are heated at 55° C for an additional 45 minutes during which time an orange precipitate, thallium iodide, forms at the bottom of the reaction vessel. This precipitate is removed by filtration and the volume of filtrate recovered reduced by rotary evaporation until substantially free of organic solvents. The oily residues remaining subsequent to such evaporation is diluted with 1.5 milliliters water and taken up in 250 milliliters chloroform. The chloroform is removed by rotary evaporation and the residue taken up in hot cyclohexane. Isopropanol is added dropwise to effect complete solution of the oily residue. Upon cooling white crystals of N-ethyl-2-bromocarbazole are recovered by filtration, yield: 18.8 grams m. p. 91°–92° C.

About 16.3 grams 0.059 moles N-ethyl-2-bromocarbazole are dissolved in 90 milliliters benzene and the resulting solution transferred to a 500 milliliter 3 neck flask equipped with a Teflon coated magnetic stirring bar, an argon gas inlet tube and a pressure equalizing addition funnel containing about 50 milliliters anhydrous ether. The contents of the flask are blanketed with argon and about 0.059 moles butyllithium in hexane added to the addition funnel. The resulting butyllithium solution is thereafter introduced into the flask with rapid stirring. After about 30 minutes the contents of the flask are tested (Gilman Color Test II) for unreacted butyllithium. After 60 minutes the solution tested negative for butyllithium but positive (Gilman Color Test I) for an aryllithium compound.

The contents of the flask (the solution containing N-ethyl-2-lithiocarbazole) is transferred to a 500 milliliter 1 neck flask equipped with a 250 milliliter pressure equalizing addition funnel. The addition funnel, which contains 4.31 grams (0.059 moles) butyllithium in dimethylformamide, 16 milliliters benzene and 4 milliliters of ether is equipped with an argon inlet tube. Preliminary to combining the contents of the addition funnel and the flask, the flask is chilled to −20° C. After the contents of the addition funnel and the flask are combined, the resulting solution turns light green in color and then a cloudy yellow. The contents of the flask are allowed to warm to room temperature and 75 milliliters of saturated ammonium chloride solution added thereto. The organic layer of the reaction mixture is washed three times with water and the combined aqueous layers extracted with benzene. All recovered organic fractions are then combined and dried over anhydrous magnesium sulfate. Upon evaporation of solvent a green oily residue remains which is subsequently crystallized. This crude product is taken up in hot cyclohexane, the volume of cyclohexane reduced until insipient crystals form from this hot solution. Yield: 5.4 grams N-ethyl-2-carboxyaldehyde m. p. 120°–123° C.

About 11.1 grams (0.05 moles) N-ethylcarbazole-2-carboxaldehyde (prepared in the manner described above) and about 3.1 grams (0.05 moles) malonitrile, 1.0 milliliters glacial acetic acid, 0.35 grams ammonium acetate, and 40 milliliters benzene are heated in a reaction vessel to boiling under reflux conditions for 30 minutes. The solvent is removed from this mixture by rotary evaporation and the recovered product recrystallized twice with glacial acetic acid. The bright yellow crystals recovered, N-ethyl-2-dicyanovinylcarbazole, are washed with ethanol and dried in a vacuum oven.

EXAMPLE IV

Preparation of N-ethyl-2-tricyanovinylcarbazole

This compound is prepared by a technique analogous to the method of McKusick et al., J. Am. Chem. Soc. 80, 2806 (1958). In this procedure, a mixture comprising about 2.58 grams (0.01 moles ) of N-ethyl-2-dicyanovinylcarbazole and about 1.3 grams (0.02 moles) potassium cynanide (which has been previously dissolved in 30 milliliters ethanol and 10 milliliters water) is stirred for a few minutes over a steam bath. To this solution is added 20 milliliters of a 10 percent solution of acetic acid. Subsequent to such addition, a precipitate forms which is recrystallized from an ethanol/water mixture. This crystalline product is dissolved in 30 milliliters of acetic acid and about 4.4 grams (0.0099 moles) lead tetraacetate added thereto. This mixture is then heated continuously on a steam bath for 2 hours, the highly colored crystalline product which forms separated by filtration and purified by recrystallization from acetic acid.

What is claimed is:

1. Compounds of the formula

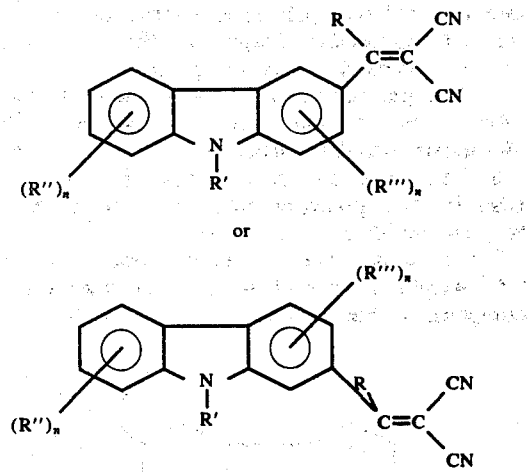

wherein R is hydrogen or nitrile; and R'; R'' and R''' are independently selected from an aliphatic hydrocarbon radical having from about 1 to about 10 carbon atoms; phenyl; or substituted phenyl, said phenyl substituents being capable of releasing electrons to relatively electron deficient centers within the compound; amino; diarylamino; dialkylamino or alkoxy; and n can range from 0 up to the potential number of positions of substitution on the aromatic ring system.

2. The compounds of claim 1, 3-dicyanovinyl-N-alkylcarbazole.

3. The compounds of claim 1, 3-tricyanovinyl-N-alkylcarbazole.

4. A photoconductive composition comprising a solid solution of at least one photogenerator compound of the formula

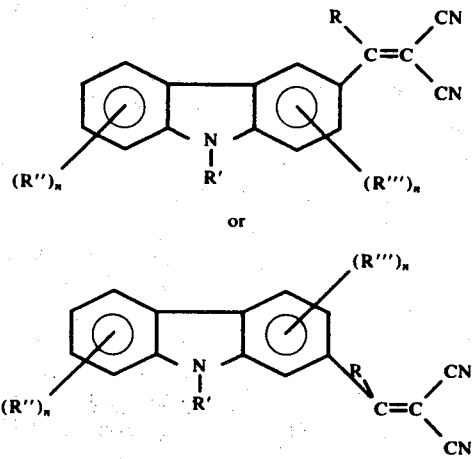

wherein R is hydrogen or nitrile; and R', R" and R'" are independently selected from an aliphatic hydrocarbon radical having from about 1 to about 10 carbon atoms; phenyl or substituted phenyl, said phenyl substituents being capable of releasing electrons to relatively electron deficient centers within the compound amino; diarylamino; dialkylamino or alkoxy; n can range from 0 up to the potential number of positions of substitution on the aromatic ring system and an insulating polymeric matrix, said polymeric matrix being capable of rapid and efficient transport of charge carriers of at least one polarity.

5. The photoconductive composition of claim 4, wherein the photogenerator compounds is a 3-dicyanovinyl-N-alkyl-carbazole.

6. The photoconductive composition of claim 4, wherein the photogenerator compound is a 3-tricyanovinyl-N-alkyl carbazole.

7. A composition comprising from about 0.1 to about 99.9 weight percent of at least one photogenerator compound of the formula

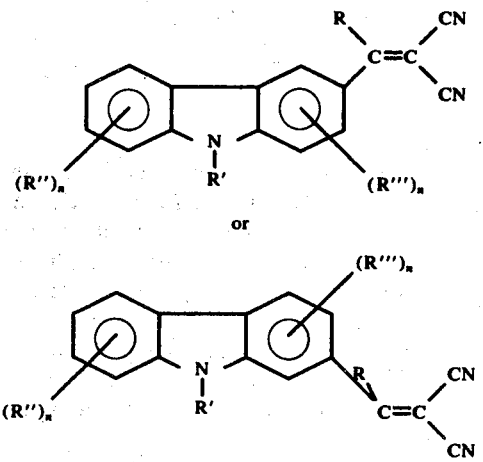

wherein R is hydrogen or nitrile; and R', R" and R'" are independently selected from an aliphatic hydrocarbon radical having from about 1 to about 10 carbon atoms; phenyl; or substituted phenyl, said phenyl substituents being capable of releasing electrons to relatively electron deficient centers within the compound amino; diarylamino; dialkylamino or alkoxy; n can range from 0 up to the potential number of positions of substitution on the aromatic ring system in an insulating polymeric matrix the minimum concentration of photogenerator compound relative to polymeric matrix being sufficient to render the composition photoconductive.

8. The composition of claim 7, wherein the photogenerator compounds is a 3-dicyanovinyl-N-alkyl carbazole.

9. The composition of claim 7, wherein the photogenerator compound is a 3-tricyanovinyl-N-alkyl carbazole.

10. An electrophotographic imaging member comprising a conductive substrate and a photoconductive insulating layer operatively disposed in relation thereto, said photoconductive insulating layer comprising a composition containing from about 0.1 to about 99.9 weight percent of at least one photogenerator compound of the formula

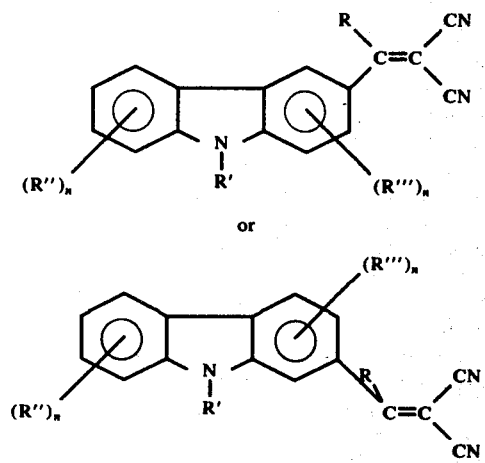

wherein R is hydrogen or nitrile; and R', R" and R'" are independently selected from an aliphatic hydrocarbon radical having from about 1 to about 10 carbon atoms; phenyl; or substituted phenyl, said phenyl substituents being capable of releasing electrons to relatively electron deficient centers within the compound amino; diarylamino; dialkylamino or alkoxy; n can range from 0 up to the potential number of positions of substitution on the aromatic ring system in an insulating polymeric matrix, the minimum concentration of photogenerator compound relative to polymeric matrix being sufficient to render the composition photoconductive.

11. The imaging member of claim 10, wherein the photogenerator compound is a 3-dicyanovinyl-N-alkyl-carbazole.

12. The imaging member of claim 10, wherein the photogenerator compound is a 3-tricyanovinyl-N-alkyl-carbazole.

13. An electrostatographic imaging process comprising a. providing an electrophotographic imaging member having a conductive substrate and a photoconductive insulating layer operatively disposed in relation thereto, said photoconductive insulating layer comprising a composition containing from about 0.1 to about 99.9 weight percent of at least one photogenerator compound of the formula

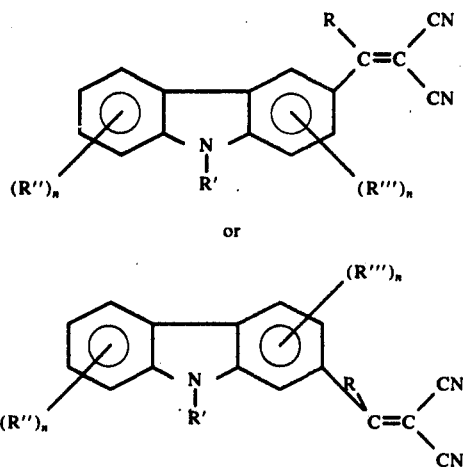

wherein R is hydrogen or nitrile; and R', R", and R''' are independently selected from an aliphatic hydrocarbon radical having from about 1 to about 10 carbon atoms; phenyl; or substituted phenyl, said phenyl substituents being capable of releasing electrons to relatively electron deficient centers within the compound amino; diarylamino; dialkylamino or alkoxy; n can range from 0 up to the potential number of positions of substitution on the aromatic ring system in an insulating polymeric matrix, the minimum concentration of photogenerator compound relative to polymeric matrix being sufficient to render the composition photoconductive; and b. forming a latent electrostatic image on said member.

14. The imaging process of claim 13, wherein the photogenerator compound is a 3-dicyanovinyl-N-alkyl-carbazole.

15. The imaging process of claim 13, wherein the photogenerator compound is a 3-tricyanovinyl-N-alkyl carbazole.

* * * * *